(12) United States Patent
Müller et al.

(10) Patent No.: US 6,379,349 B1
(45) Date of Patent: *Apr. 30, 2002

(54) ARRANGEMENT FOR ELECTROTHERMAL TREATMENT OF THE HUMAN OR ANIMAL BODY

(75) Inventors: Gerhard Müller; Kai Desinger, both of Berlin (DE)

(73) Assignee: Celon AG medical instruments, Teltow (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,146
(22) PCT Filed: Nov. 7, 1996
(86) PCT No.: PCT/DE96/02164
  § 371 Date: May 8, 1998
  § 102(e) Date: May 8, 1998
(87) PCT Pub. No.: WO97/17009
  PCT Pub. Date: May 15, 1997

(30) Foreign Application Priority Data

Nov. 8, 1995 (DE) ............................. 195 41 566

(51) Int. Cl.⁷ ................................. A61B 18/18
(52) U.S. Cl. .................... 606/41; 606/46; 606/48; 606/50; 607/101

(58) Field of Search ............. 606/41–50; 604/22; 607/101, 102

(56) References Cited

U.S. PATENT DOCUMENTS

| 5,500,012 A | | 3/1996 | Brucker et al. | |
| 5,720,718 A | * | 2/1998 | Rosen et al. | 604/22 |

FOREIGN PATENT DOCUMENTS

| WO | WO 81/03272 | 11/1981 |
| WO | WO 94/02077 | 2/1994 |
| WO | WO 96/18349 | 6/1996 |
| WO | WO 98/19613 | 5/1998 |

* cited by examiner

*Primary Examiner*—Linda C. M. Dvorak
*Assistant Examiner*—David M. Ruddy
(74) *Attorney, Agent, or Firm*—Venable; Robert Kinberg

(57) ABSTRACT

An arrangement (1) for electrothermally treating the human body or an animal body, in particular for tissue coagulation or electrotomy, includes two electrodes (3, 4) for insertion into the body to be treated. The two electrodes (3, 4) are electrically insulated from each other and are disposed at a distance from each other to produce an electric or electromagnetic field heating the body tissue in the treatment area, and each electrode is connected by a feed line with a power source arranged outside the body. An elongate catheter (2) is provided for joint insertion of the two electrodes (3, 4) into the body, which are staggered in relation to each other in the axial direction of the catheter (2) and connected to the catheter (2) or a component thereof.

19 Claims, 5 Drawing Sheets

ARRANGEMENT FOR ELECTROTHERMAL TREATMENT OF THE HUMAN OR ANIMAL BODY

BACKGROUND OF THE INVENTION

The invention relates to an arrangement for the electrothermal treatment of the human or animal body, in particular for the electrocoagulation or electrotomy.

The use of high-frequency alternating currents in the frequency range of 300 kHz to 2 MHZ for tissue coagulation and tissue separation has long been known in the field of surgery, resulting in the treated tissue being coagulated or vaporized, which is referred to as electrocoagulation or electrotomy. A distinction must be made here between the monopolar and the bipolar HF thermotherapy.

For the monopolar thermotherapy, an electrode—also referred to as the neutral electrode—is configured as a large-surface patient lead and is installed near the place of incision on the patient. The shape of the actual working electrode—referred to as the active electrode—is adapted to the respective application. Thus, large-surface sphere, disk or needle electrodes are used for the tissue coagulation, whereas thin lancet or loop-type electrodes are used for tissue separation.

In the bipolar HF thermotherapy, on the other hand, both electrodes are arranged in close proximity to the place of incision, so that the effect of the alternating current is limited to the area immediately surrounding the place of incision, thereby resulting in a high degree of safety for the patient and the user since accidents caused by capacitive leakage currents or burning at the neutral electrode can no longer occur. Another advantage of the bipolar HF thermotherapy consists in the considerably lower load resistance of the tissue between the two electrodes, which permits a reduction in the necessary generator output while maintaining the thermal effect.

Based on the position of the electrodes, the HF thermotherapy can furthermore be divided into the surface coagulation on the one hand and the depth coagulation on the other hand.

The bipolar technique uses two parallel-arranged tactile electrodes for the surface coagulation, which are placed onto the tissue surface. As a result of this, the tissue underneath is heated, owing to the flow of current, and is thus coagulated.

The use of needle, lancet, or loop-type electrodes for the monopolar electrotomy is known in the field of depth coagulation. Electric arcs must be generated for this on the active electrode in order to vaporize the tissue, positioned in front of the active electrode, thereby realizing a tissue cut. This is relatively simple with the monopolar technique because only a specific field strength is required to trigger a spark discharge at the active electrode. The bipolar technique makes higher demands on the design of the electrode configuration since the physical processes in this case cannot be controlled as easily. That is why only a few bipolar electrode arrangements for the depth coagulation are known, e.g. the bipolar needle electrode, which is suitable, among other things, for the myoma therapy. This known bipolar electrode arrangement consists of two parallel-arranged needle electrodes that are stuck into the tissue, by means of which the tissue between the electrodes is heated as a result of the current flow and is thus coagulated.

However, the known bipolar electrode arrangements for the depth coagulation have the disadvantage that placement of the electrodes through two puncture sites is relatively involved. Furthermore, the predetermination of the field distribution by the user is relatively imprecise because the position of the two electrodes relative to each other generally cannot be specified exactly.

The DE 43 22 955 A1 furthermore discloses the use of laser radiation for the coagulation of body tissue, which laser radiation can be transmitted into the therapy region via a cylindrical optical waveguide, wherein the known optical waveguide additionally permits the transmission of ultrasound energy, so that the two therapy methods of ultrasound tissue separation and the laser coagulation can be combined.

A waveguide is also disclosed in the DE 44 32 666 A1, which makes it possible to transmit high-frequency energy in addition to ultrasound waves and laser radiation, so that the initially mentioned methods of high frequency surgery can be used at the same time as the laser surgery and the ultrasound surgery. For this, the known waveguide has a cylindrical design and additionally comprises two layers of an electrically conductive material for the high-frequency transmission, which layers are also cylindrical and are electrically insulated against each other. Thus, the known waveguide permits the transmission of high-frequency energy from a high-frequency generator, arranged extracorporeal, into the therapy region, but it does not permit the release of the high-frequency energy to the body tissue.

SUMMARY OF THE INVENTION

It is thus the object of the invention to create an arrangement for the electrothermal treatment of the human or animal body, which permits an interstitial tissue coagulation by means of a bipolar electrode arrangement and which avoids the aforementioned disadvantages of the known types of arrangements.

The invention includes the technical teaching that a bipolar electrode arrangement is used for the thermotherapy, the two electrodes of which are arranged one after another on an elongated catheter to make it possible to insert the two electrodes jointly into the body through a single puncture site, wherein the two electrodes are connected to the catheter or form a component of the catheter.

Herewith and in the following, the term catheter is understood to have a general meaning. It is not limited to the preferably used hollow-cylindrical arrangements, described in detail in the following, but can also be realized with large arrangements of nearly optional cross sections. Critical to the function according to the invention is only that the two electrodes are inserted jointly into the patient's body, through one puncture site.

The catheter according to the invention for the first time allows placing the electrodes into deep tissue layers and obtaining a partial tissue coagulation there.

The electrodes in the arrangement according to the invention are connected to a current source that supplies the electrical energy necessary for heating up the tissue. The term current source here is not limited to narrowly defined sources having a constant current, but includes also the preferably used alternating current generators, especially high-frequency generators.

One advantageous variant of the invention provides that the axial distance between the two electrodes can be adjusted, so that the field distribution can be varied. If the insulator length in axial direction between the two electrodes is shorter, for example, than twice the electrode diameter, spherical coagulation necroses can be obtained advantageously, whereas the shape of the coagulation necroses for longer insulator lengths is more oval.

The preferred embodiment of this variant therefore provides that the proximal electrode has a hollow design, at least at its distal end, such that it can accommodate the distal electrode on its inside. The external cross section of the distal electrode is smaller than the internal cross section of the proximal electrode to allow an axial displacement of the distal electrode inside the proximal electrode. It is important in this case for the two electrodes to be electrically insulated against each other in a suitable manner, since the two electrodes can overlap in axial direction. An electrical insulation is provided for this on the inside of the proximal electrode or on the outside of the distal electrode. For example, this insulation can consist of a dielectric coating or an insulating material sleeve, preferably composed of PTFE or polyimide—as in the initially listed reference DE 44 32 666 A1—wherein the cross section for the insulating-material sleeve is preferably adapted to the cross section of the distal or proximal electrode, such that the insulating-material sleeve can be press-fitted to the proximal or distal electrode and is thus fixed on the electrode. Thus, the two electrodes are coaxially arranged and can be displaced against each other in axial direction, so that the field distribution can be changed, wherein a section of the distal electrode in longitudinal direction is held inside the proximal electrode.

In this variant of the invention, as for the other variants of the invention, the two electrodes have a cylindrical cross section, wherein the internal diameter of the proximal electrode for this variant must be larger than the external diameter of the distal electrode, so that the distal electrode can be displaced in axial direction. However, the invention is not limited to cylindrical electrode designs, but can be realized with other electrode cross sections as well. Concerning the function of this variant of the invention, it is only critical that the internal cross section of the proximal electrode is adapted to the external cross section of the proximal electrode in such a way that the distal electrode can be displaced in axial direction inside the proximal electrode in order to change the axial distance between the two electrodes.

In another variant of the invention, the adjustment of the axial distance between the two electrodes is made possible with an elongated carrier element of electrically insulating material, which is arranged such that it can be displaced inside the proximal electrode and contains the distal electrode on the side in its distal region. The proximal electrode is therefore designed to be hollow, at least at its distal end, to be able to hold the carrier element. The internal cross section of the proximal electrode in this case is adapted to the external cross section of the carrier element, such that the carrier element can be displaced in axial direction in order to be able to adjust the axial distance between the distal end of the proximal electrode and the distal electrode, arranged on the carrier element. In this variant of the invention, the distal electrode is attached to the side of the electrically insulating carrier element and can consist, for example, of a ring-shaped, metallic coating or a metallic sleeve, which is pushed axially onto the carrier element during the assembly and is press-fitted to this carrier element.

In accordance with another variant of the invention, the spacing between the two electrodes is specified, to achieve a simple design for the catheter and to ensure a predetermined field distribution. For this, the catheter also has an elongated carrier element of electrically insulating material, with the electrodes fixedly attached to the side in axial direction and at a distance to each other. On the one hand, the carrier element here is used for a mechanical fastening of the electrodes, in order to achieve a predetermined field distribution as a result of the constant distance between the electrodes. On the other hand, the carrier element must insulate the two electrodes electrically against each other and is therefore composed of an electrically insulating material. In the preferred embodiment of this variant, the carrier element has a cylindrical cross section, wherein the two electrodes have a hollow-cylindrical design and are arranged so as to be circumferential with respect to the longitudinal axis of the carrier element. In this case, the electrodes can be deposited, for example, on the carrier element surface as a metallic coating, or they can respectively form a metallic sleeve that is fitted onto the carrier element and is press fitted to it.

In another embodiment of this variant, the electrodes are not fixed axially as a result of being arranged on a carrier element, but through respectively one connecting element between the electrodes, which connects the fronts of the electrodes. In addition to the axial fixation of the electrodes, the connecting element must also insulate the two electrodes against each other and thus consists of an electrically insulating material. The electrodes and the connecting pieces in this case are preferably cylindrical and have the same cross section, so that the outside contour of the catheter is continuous, without projecting edges, at the transitions between the electrodes and the connecting elements. This is very important for the insertion of the catheter into the body of the patient, to avoid unnecessary injuries.

A modified variant of the invention provides for more than two electrodes, which are arranged at a distance to each other in axial direction of the catheter. As described in the above, the electrodes can be attached to the side of an elongated carrier element or, as previously explained, can respectively be separated from each other with the aid of a connecting element of electrically insulating material.

The preferred embodiment of this variant provides that the individual electrode pairs, arranged such that they are distributed axially along the longitudinal axis of the catheter, can be actuated separately and have separate feed lines for this, which are preferably extended out of the body through a hollow conduit inside the catheter and can be connected to an adequate control device that permits an individual adjustment of, for example, current, voltage and/or frequency. As a result of the superimposition of the fields generated by the individual electrode pairs, it is possible in this way to specify the field distribution freely within far-ranging limits, e.g. to destroy as little healthy tissue as possible during an electrocoagulation. In one advantageous modification of this variant, the extracorporeal control device has several storage elements, in which the electrical parameters such a current, voltage and frequency for various field distributions are stored, so that the user must only select the desired field distribution, whereupon the control device then reads out the electrical parameters necessary for reaching this field distribution from the respective storage element and respectively actuates the individual electrode pairs.

Other advantageous modifications of the invention are shown in further detail in the following with the aid of the figures and together with the description of the preferred embodiment of the invention.

DESCRIPTION OF THE PREFERRED EMBODIMENTS

Figure 1:
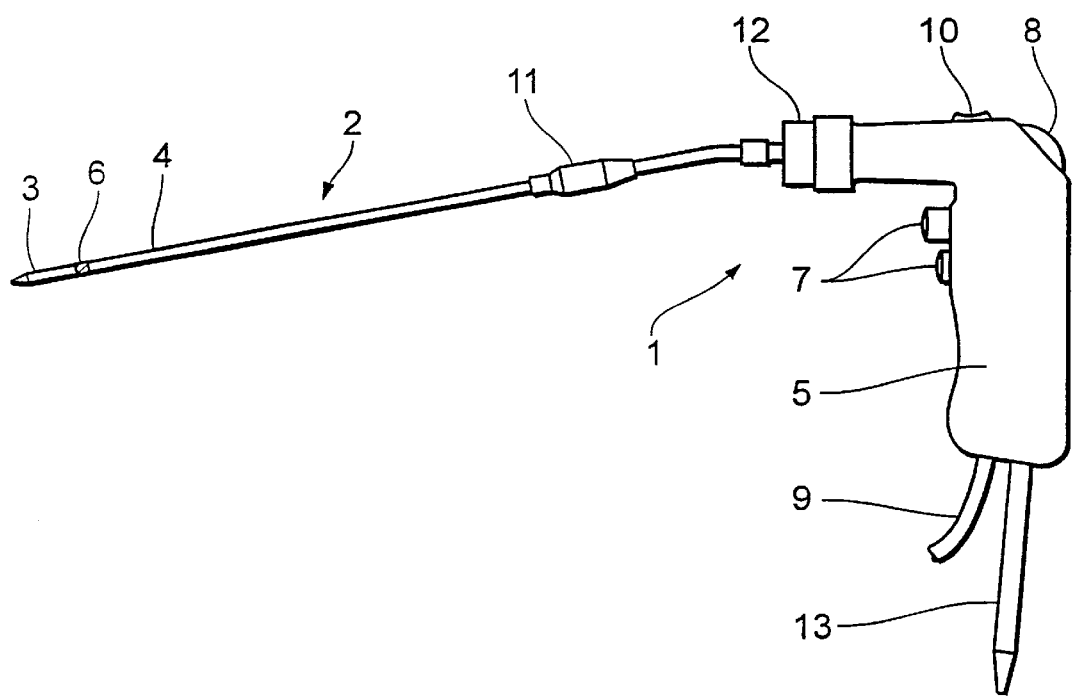
FIG. 1 illustrates preferred embodiment of the invention, depicting an arrangement for electrothermal treatment with a catheter for inserting the electrodes into the body and a manipulator for guiding the catheter.
Figure 2A:
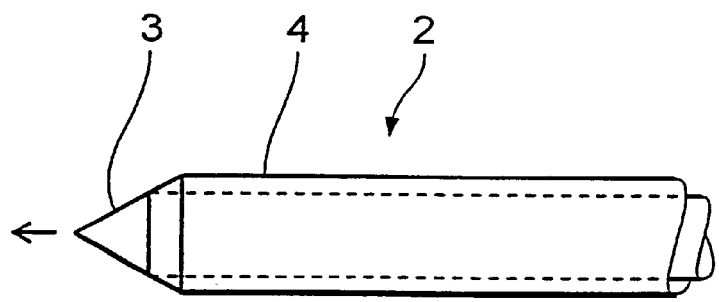
FIGS. 2a and 2b illustrate the catheter for the arrangement in FIG. 1, with a core electrode inserted and pulled out.
Figure 2B:
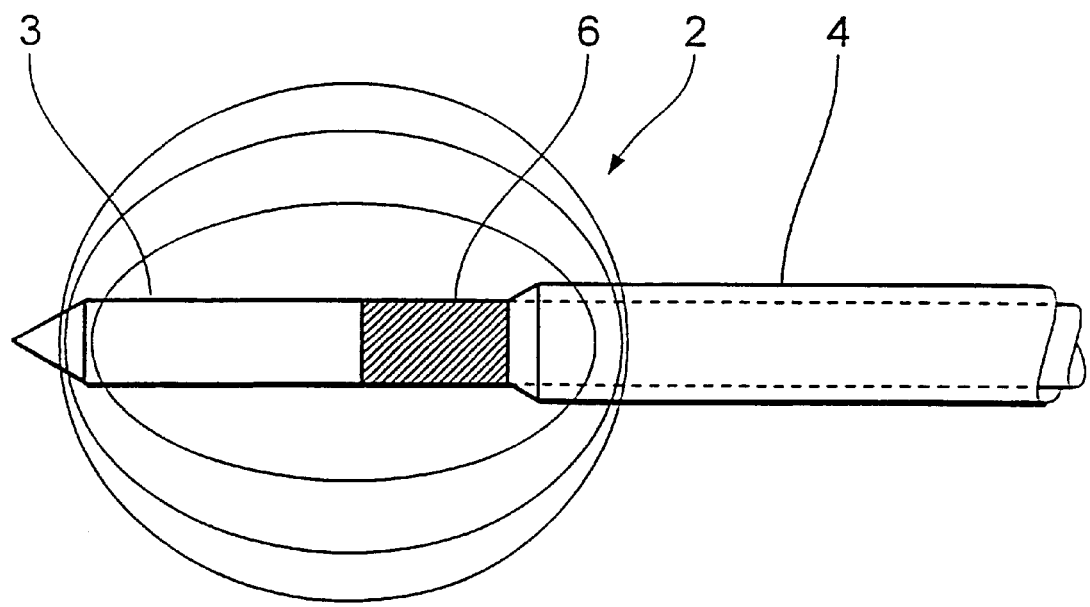

As a preferred embodiment of the invention, FIG. 1 shows an arrangement 1 for the electrothermal treatment of the human and animal body, consisting essentially of a catheter 2 with a core electrode 3 and a covering electrode 4, as well as a manipulator or handle 5 for guiding the catheter 2, wherein the catheter 2 is shown in further detail in the FIGS. 2a and 2b.

The catheter 2 permits an adjustment of the axial distance between the two electrodes 3, 4, so that the field distribution in the therapy region can be specified. For this, the catheter 2 has the cylinder-shaped, stainless steel core electrode 3 with a diameter of 800 $\mu$m. Except for its distal end, the surface area of said electrode is covered with a 50 $\mu$m thick coating of polyimide 6 as electrical insulation. This coated core electrode 3 is positioned such that it can be displaced coaxially in the hollow cylindrical covering electrode 4, also made of stainless steel, and has an internal diameter of 900 $\mu$m. The external diameter of the covering electrode 4 is 1500 $\mu$m for a length of 10 cm. It thus a large length-to-diameter ratio, about 67.

With the aid of a displacement mechanism, integrated into the manipulator 5, the internal core electrode 3 can be pulled back before the catheter 2 punctures the tissue, so that the core electrode 3 and the covering electrode 4 together form a symmetrically ground puncturing spike, as shown in FIG. 2a.

After inserting the catheter 2 into the tissue, the core electrode 3 can be extended in axial direction and thus forms a dipole configuration with the insulating polyimide layer 6 and the covering electrode 4, as shown in FIG. 2b. The axial displacement of the core electrode 3 furthermore allows an adjustment of the axial distance between the two electrodes 3, 4 and thus a concerted influencing of the field distribution in the therapy region. The displacement mechanism for the core electrode 3 is operated via a push-button rocker 7, which is integrated into the manipulator 5 that is shaped like a pistol grip for ergonomic reasons. The manipulator 5 furthermore contains a switch 8 for connecting the electrode arrangement to an HF generator, which is connected to the manipulator 5 via an electrical feed line 9. The manipulator 5 also contains a release mechanism 10, with which the core electrode 3 can be released and subsequently pulled axially from the covering electrode 4. Following the release of a locking mechanism 11, the covering electrode 4 can also be pulled out axially. By separating the electrodes 3, 4 from the manipulator 5, it is easily possible to sterilize and subsequently reuse the electrodes 3, 4.

The catheter 2, comprising the core electrode and the covering electrode 3, 4, is connected to the manipulator 5 via a rotatable bearing 12 for holding and, owing to its angled form, permits an operation that is adapted to the field of vision of the physician, e.g. as is necessary for the turbinal coagulation.

The illustrated arrangement 1 furthermore allows introducing a rinsing liquid into the tissue in the therapy region, in order to improve the electrical coupling. In this way, it is possible to balance the loss of liquid that occurs during coagulation, which otherwise leads to a change in the electrical impedance of the tissue in the therapy region and worsens the electrical coupling. The manipulator 5 therefore determines the tissue impedance from the applied voltage and the current via the electrodes 3, 4 and releases a corresponding amount of rinsing liquid to the tissue in order to keep the tissue impedance constant. The rinsing liquid is supplied by a separate rinsing pump via a hose 13 to the manipulator 5 and is pumped through the hollow covering electrode 4 into the therapy region. There, the rinsing liquid exits through a gap between core electrode 3 and covering electrode 4 into the tissue.

Figure 3A:
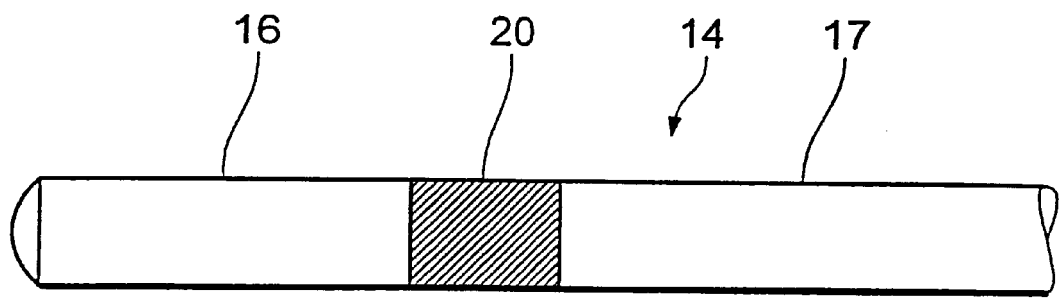
FIGS. 3a and 3b illustrate various catheters with fixed electrodes for obtaining a specified field distribution.
Figure 3B:
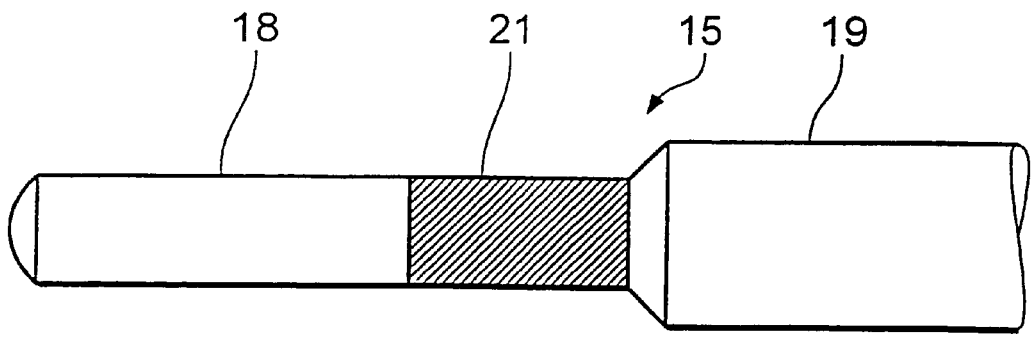

The FIGS. 3a and 3b respectively show a catheter 14 or 15, having a proximal electrode 17 or 19 and a distal electrode 16 or 18, wherein the spacing between the two electrodes 16, 17 or 18, 19 is constant in order to reach a specified field distribution and to permit a simple design for the catheter 14, 15. The two electrodes 16, 17 or 18, 19 in this case have a cylindrical design and are mechanically connected on their fronts with the aid of an also cylindrical connecting element 20 or 21 of electrically insulating material, wherein the connecting element 20 or 21, as well as the proximal electrode 17 or 19 is provided with an axially extending hollow conduit to hold the electrode feed line. The external cross sections of the two electrodes 16, 17 and the cross section of the connecting element 20 are identical in catheter 14, shown in FIG. 3a, so that the outside contour of the catheter 14 is smooth even at the transition points between the electrodes 16, 17 and the connecting element 20, thereby making it easier to insert the catheter 14 into the body of the patient. In contrast, the proximal electrode 19 for the catheter 15, shown in FIG. 3b, has a larger cross section than the distal electrode 18 and the connecting element 21, wherein the proximal electrode 19 is conically tapered to match the cross section of the connecting element 21 at the transition point to the connecting element 21.

Figure 4:
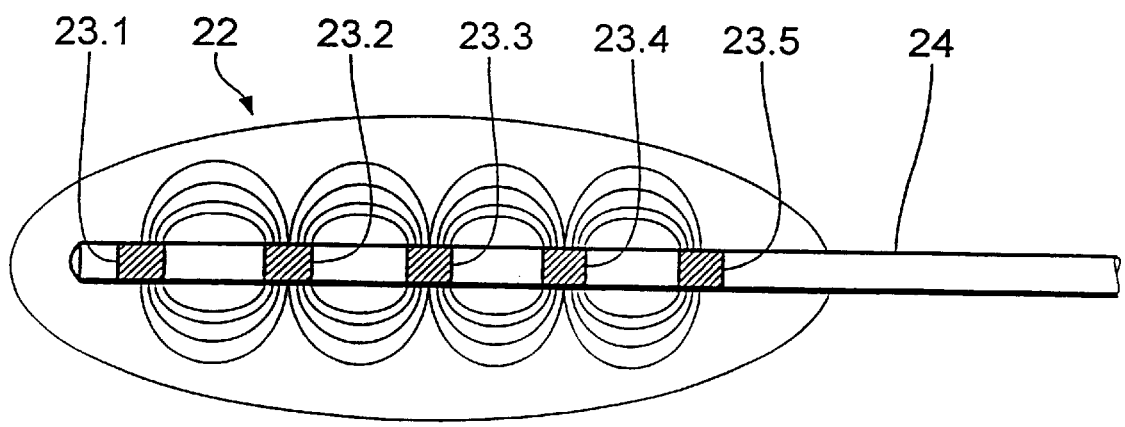
FIG. 4 illustrates a catheter with five electrodes, making it possible to have special field distribution forms.

The FIG. 4 also shows a catheter 22 that essentially distinguishes itself from the above-described catheters in that it has a larger number of electrodes 23.1 to 23.5, which are arranged along the longitudinal axis of the catheter 22 and are essentially composed of ring-shaped, metallic coatings, deposited on the surface area of a cylinder-shaped carrier element 24 of electrically insulating material. The electrodes 23.1 to 23.5 are respectively contacted separately via feed lines, which are placed in an axially extending hollow conduit of the carrier element. For one thing, the larger number of electrodes 23.1 to 23.5 makes it possible to reduce the partial current density at the electrodes 23.1 to 23.5, thereby preventing the temperature from increasing too much. For another thing, it is possible to generate a field distribution that differs from the one for only two electrodes by superimposing the individual fields. In addition, it is possible to purposely influence the field distribution by switching individual electron pairs on or off.

Figure 5:
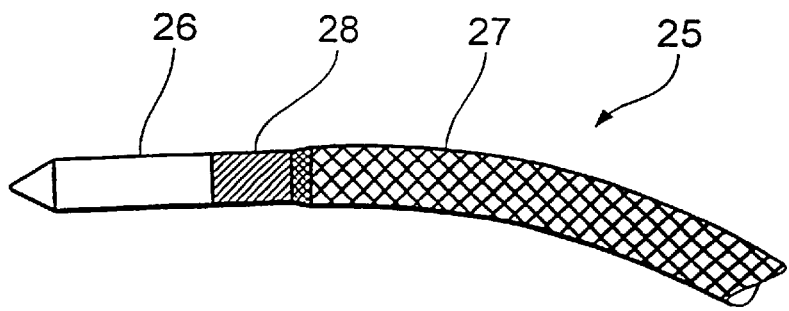
FIG. 5 illustrates a flexible catheter for use in the minimally invasive surgery.

In another embodiment of the invention, FIG. 5 illustrates a catheter 25, which is flexible and thus insertable insertion even into body cavities with bent inlet conduits, which is particularly important for the minimally invasive medicine (MIM). The catheter 25 essentially consists of a cylindrical core electrode 26 of spring steel wire, which is surrounded by covering electrode 27 in the shape of a hollow cylinder and formed from a flexible metal braid. The surface area of the core electrode 26 is provided with an electrically insulating coating 28, except for its distal end, which coating is designed to insulate the two electrodes 26, 27 against each other.

Figure 6A:
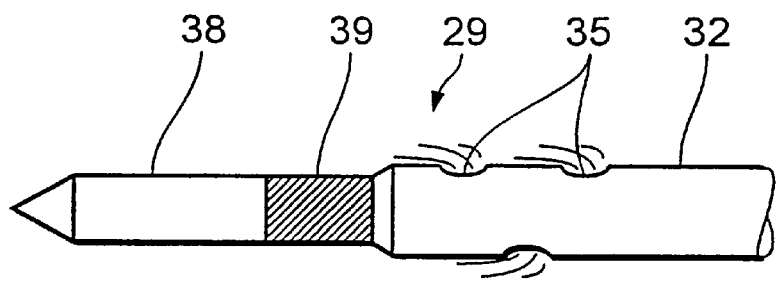
FIGS. 6a, 6b, and 6c illustrate various catheters making it possible to feed rinsing liquid.
Figure 6B:
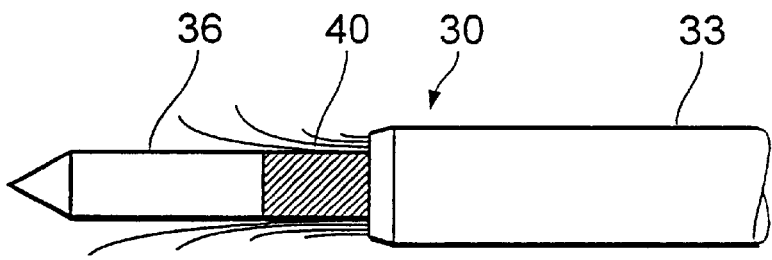
Figure 6C:
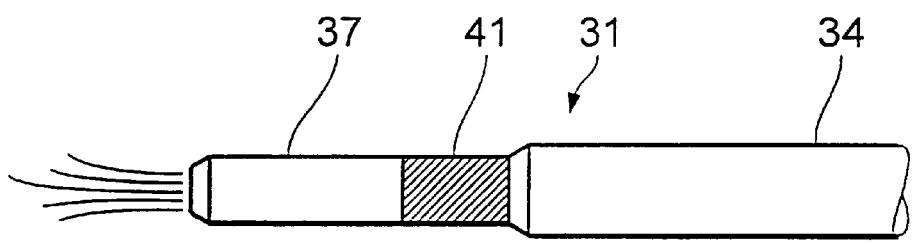

The FIGS. 6a, 6b and 6c show additional advantageous embodiments of catheters 29, 30, 31 with respectively one hollow-cylindrical, proximal covered electrode 32, 33, 34 and one cylinder-shaped, distal core electrode 36, 37, 38. With the illustrated catheters 29, 30, 31 it is advantageously possible to deliver rinsing liquid to the tissue, in order to balance the loss of liquid in the tissue during the coagulation and a therewith connected worsening of the electrical coupling. The rinsing liquid in this case is delivered through an axially extending hollow conduit in the proximal covered electrode 32, 33, 34 and delivery is ensured by a rinsing liquid pump, arranged extracorporeal. However, the release of the rinsing liquid in the therapy region occurs in different ways for the illustrated catheters 29, 30, 31. The catheter 29, shown in FIG. 6a, is therefore provided with several distally arranged openings 35 in the surface area of the covering electrode 32, through which the rinsing liquid can exit from the hollow conduit into the tissue. In contrast, with the catheter 30, shown in FIG. 6b, the rinsing liquid exits through a gap between covering electrode 33 and core electrode 36 into the tissue. The catheter 31, shown in FIG. 6c, on the other hand has a continuous hollow conduit in axial direction, which also extends through the core electrode 37 and ends at the distal front of core electrode 37, so that the rinsing liquid is discharged into the tissue at the distal front of distal electrode 37.

A physiological salt solution is preferably used as rinsing liquid, which ensures a good electrical coupling with the tissue and reduces the danger of tissue carbonization by limiting the temperature to <100° C. In this case, the two electrodes 32, 38 or 36, 33 or 34, 37 are also insulated against each other through a coating 39, 40, 41 of electrically insulating material that is deposited on the core electrode 36, 37, 38.

Instead of the feed line for the rinsing liquid, the hollow conduit for the catheter 31, shown in FIG. 6c, can also hold an optical waveguide for a modified optical biopsy, which permits a precise positioning of the catheter 31 in the therapy region through a measuring of the backscatter signal or the tissue fluorescence during X-rays. In addition, a laser transmission through an integrated optical waveguide also offers the option of measuring the blood flow through Doppler measurement, depending on the wavelength used. Furthermore, the laser radiation transmitted via such an optical waveguide into the therapy region can then be used for the thermo-optical tissue coagulation. Finally, the hollow conduit also permits the positioning of a temperature sensor for the coagulation control.

Figure 7:
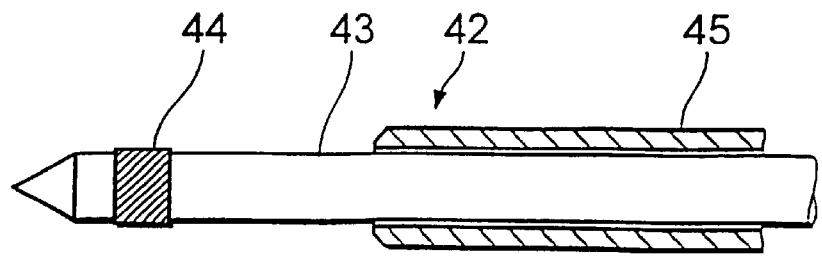
FIG. 7 illustrates another catheter with adjustable electrode spacing.

FIG. 7 finally shows another catheter 42, which permits the adjustment of the electrode spacing so that it is possible to influence the field distribution in the therapy region. For this, the illustrated catheter 42 has a cylindrical carrier element 43 of electrically insulating material, comprising at its distal end a distal electrode 44 that is deposited on the side as a ring-shaped metallic coating.

This carrier element 43 is guided by a proximal electrode 45 with a hollow-cylinder design, wherein the external diameter of the carrier element 43 is smaller than the internal diameter of the proximal electrode 45, so that the carrier element 43 with the distal electrode 44 can be displaced in axial direction to adjust the electrode spacing. At its distal end, the carrier element 43 is ground such that it forms a puncturing spike for inserting the catheter 42 into the body of the patient.

The design of the invention is not limited to the aforementioned, preferred embodiments. Rather, a number of variants are conceivable, which make use of the depicted solution, even if the embodiments are totally different.

What is claimed is:

1. An arrangement for use with a power source to electrothermally treat a body, comprising:

a manually graspable handle having a handle height dimension, a handle width dimension, and a handle thickness dimension, one of the dimensions being a greatest handle dimension;

a catheter having a substantially straight portion and a longitudinal axis that runs through the substantially straight portion, the substantially straight portion including a first electrode and a second electrode that are insulated from one another and that are jointly inserted into the body, the first and second electrodes having longitudinal axes that coincide with the longitudinal axis of the substantially straight portion, the second electrode having a width that is at least as large as the width of the first electrode;

means for joining the catheter to the handle; and means for connecting both electrodes of the catheter to the power supply, wherein the substantially straight portion has a length that is at least as large as the greatest handle dimension, and has a ratio of the length to the width of the second electrode that is large, and wherein the catheter has a tip and the first electrode is disposed at the tip, the first electrode having a length that is substantially smaller than the length of the second electrode.

2. An arrangement according to claim 1, wherein the second electrode is tubular, wherein at least a portion of the first electrode is disposed inside the second electrode, and wherein the first electrode is movable with respect to the second electrode.

3. An arrangement according to claim 1, wherein the first electrode has an end, wherein the second electrode has an end, and wherein the substantially straight portion further comprises an insulating connecting element that is disposed between the first and second electrodes, the insulating connecting element being connected to the end of the first electrode and to the end of the second electrode.

4. An arrangement according to claim 1, wherein the substantially straight portion further comprises an elongated insulating carrier element, and wherein the first and second electrodes comprise conductive bands affixed to the carrier element.

5. An arrangement according to claim 1, wherein the catheter is flexible, and wherein the second electrode comprises a flexible braid.

6. An arrangement according to claim 1, wherein the substantially straight portion further comprises an elongated insulating carrier element, wherein the first electrode comprises a conductive band affixed to the carrier element, and wherein the second electrode comprises a tubular member through which the carrier element extends.

7. An arrangement according to claim 1, wherein at least one of the first and second electrodes has a channel for passage of liquid.

8. An arrangement according to claim 1, wherein the second electrode is tubular, wherein at least a portion of the first electrode extends inside the first electrode, and wherein the first and second electrodes are separated by gap for passage of liquid.

9. An arrangement according to claim 1, wherein the first and second electrodes are cylindrical and have diameters that are substantially the same, except at a tip end of the first electrode.

10. An arrangement according to claim 1, wherein the second electrode has a length that is greater than at least one of the dimensions of the handle.

11. An arrangement according to claim 1, wherein the second electrode has a length that is at least as large as the greatest handle dimension.

12. An arrangement for electrothermally treating a human or animal body, comprising:

an elongated cylindrical catheter having a tapered tip to facilitate insertion of the catheter into the body, the catheter including insulating element and first and second coaxially arranged cylindrical electrodes that are electrically insulated from one another by the insulating element and that are jointly inserted into the body, the first and second electrodes being connected to an extracorporal power source via separate feed lines to generate an electrical or electromagnetic field that heats tissue of the body in a treatment region, wherein the first and second electrodes are displaced in an axial direction with respect to each other by a fixed distance of twice the diameter of the catheter or less, wherein the first electrode is disposed at the tip of the catheter, and is substantially shorter than the second electrode, and wherein the second electrode, the insulating element, and most of the first electrode have outer diameters that are substantially constant.

13. An arrangement according to claim 12, wherein the second electrode, the insulating element, and most of the first electrode have an outer diameter of about 1500 $\mu$m.

14. An arrangement according to claim 12, wherein the insulating element comprises an elongated connecting element, and wherein the first and second electrodes are affixed to the connecting element at spaced apart positions.

15. An arrangement according to claim 12, wherein the insulating element comprises an elongated connecting element, wherein one of the first and second electrodes is affixed to the connecting element, and wherein the other of the first and second electrodes has a hollow portion in which the connecting element is received.

16. An arrangement according to claim 12, wherein the insulating element comprises a connecting element having an end that is connected to one of the first and second electrodes and another end that is connected to the other of the first and second electrodes.

17. An arrangement according to claim 12 wherein the insulating element comprises an optical waveguide, and wherein one of the first and second electrodes comprises an electrically conductive coating on the optical waveguide.

18. An arrangement according to claim 12, wherein the first electrode has a length, and the second electrode has a length that is a multiple of the length of the first electrode.

19. An arrangement according to claim 18, wherein the multiple is substantially greater than one.

* * * * *